United States Patent [19]
Barrett et al.

[11] Patent Number: 5,735,900
[45] Date of Patent: Apr. 7, 1998

[54] METHOD OF SEALING AN INTERFACE BETWEEN AN ARTICULATING PROSTHESIS AND BONE

[75] Inventors: David Barrett, London; Gordon Blunn, Bedfordshire; William Muirhead-Allwood, London; Peter Stanley Walker, Middlesex, all of England

[73] Assignee: University College London

[21] Appl. No.: 619,721

[22] PCT Filed: Oct. 19, 1994

[86] PCT No.: PCT/GB94/02284

§ 371 Date: Mar. 21, 1996

§ 102(e) Date: Mar. 21, 1996

[87] PCT Pub. No.: WO95/10990

PCT Pub. Date: Apr. 27, 1995

[30] Foreign Application Priority Data

Oct. 21, 1993 [GB] United Kingdom ............ 9321700

[51] Int. Cl.$^6$ .......................................... A61F 2/30
[52] U.S. Cl. ............................................... 623/18
[58] Field of Search .......................... 623/16, 18, 19, 623/20, 22, 23

[56] References Cited

U.S. PATENT DOCUMENTS

| 4,731,088 | 3/1988 | Collier | 623/22 |
| 4,822,368 | 4/1989 | Collier | 623/22 |
| 5,514,182 | 5/1996 | Shea | 623/18 |

*Primary Examiner*—Debra S. Brittingham
*Attorney, Agent, or Firm*—Burns, Doane Swecker & Mathis LLP

[57] ABSTRACT

A method of fitting orthopaedic prostheses is disclosed in which a semi-permeable microporous membrane is fitted over an implanted prosthesis so as to cover the junction between the prosthesis and the bone. In this way, particles generated by mechanical wear of the prosthesis are excluded. Such particles are believed to inhibit bone regeneration in the region of the prosthesis. In addition, by preventing the ingress of fibrous connective tissue cells, a secondary seal of new bone will form between the membrane and the original bone.

6 Claims, 2 Drawing Sheets

METHOD OF SEALING AN INTERFACE BETWEEN AN ARTICULATING PROSTHESIS AND BONE

This application is a 371 of PCT/GB94/02284 filed Oct. 19, 1994.

BACKGROUND OF THE INVENTION

1. Field of the Invention

This invention is directed to bone implants and in particular to prosthesis for total joint replacement.

2. Discussion of Related Art

Total joint replacement is now becoming a commonplace method of treating disorders, such as acute arthritis, where the diseased joint is removed surgically and replaced with an artificial joint. As such operations have become more common, problems arising from long-term wear of such joints have become apparent. In a number of instances, it is found that bone resorption occurs in the region of the implant which leads to the loosening of the implant in the bone canal, and the breakdown of any cement mantle between the implant and the bone canal.

Various suggestions have been made as to the cause of such degeneration. It is believed that a primary reason for this loosening is the ingress of wear particles, generated by prolonged movement of the articulating surfaces of the joint and that such particles migrate from the area of articulation into the junction between the implant and the bone. It is believed that wear particles generated in this way at the articulating surfaces migrate along the cement/metal interface (or between the bone and the implant), and cause endosteal erosion. Progressive erosion ultimately causes breakdown of the cement mantle or sufficient loosening of a cement-less stem such that it can become displaced from the bone canal or socket.

OBJECTS AND SUMMARY

It is a primary object of the present invention to provide a means for overcoming this problem and to enable total joint replacement prostheses to have a longer effective life.

According to one aspect of the present invention, there is provided a method of sealing the interface between a prosthesis and a bone, in which the prosthesis is implanted, which method comprises applying a membrane over the junction between the prosthesis and the bone, said membrane having a microporous structure whereby liquids are able to pass through the membrane but wear particles generated by articulation of the prosthesis are excluded.

Preferably, the microporous membrane has openings which are sized so as to exclude connective tissue cells, whereby bone regeneration under the membrane is also encouraged.

Since the membrane is installed essentially permanently in the area of the prosthesis, the membrane should be one which is highly bio-compatible and essentially inert to body fluids. Examples of suitable polymer materials include silicone polymers, polyurethane, polyethylene, polyesters, polypropylene, polyacrylates and methacrylates and fluorinated olefins, especially perfluorinated olefins, e.g. perfluorinated ethylene and propylene. Polytetrafluoroethylene is currently preferred. Methods of producing microporous polymer membranes of this type are known and are described, for example, in U.S. Pat. Nos. 3,953,566 & 4,187,390. An example of one commercially available product is the microporous polytetrafluoroethylene material manufactured by W. L. Gore & Associates Limited, under the trade mark "GORE-TEX ePTFE". This material has been used successfully in the past as a suture material and also for periodontal material, to encourage bone growth in the area of tooth roots where the gums are regressed. The wear particles produced by articulation of the joint are generally small particles of metal or plastics material of micron or sub-micron size and the pore size in the membrane material should be selected so as to exclude particles of such sizes. The above cited U.S. Patents give details of how such microporous materials can be manufactured and its disclosure is specifically incorporated herein. The membrane may be a single sheet material or a laminate.

The invention will now be illustrated with reference to the accompanying drawings, describing the application of the invention to a total hip replacement prosthesis, although it will be appreciated that the invention may also be applied to other joints, including those in which no articulation takes place. The method and procedure of the present invention may be applied to both cemented and cementless (press-fit) implants.

BRIEF DESCRIPTION OF THE DRAWINGS

In the accompanying drawings.

DETAILED DESCRIPTION OF THE PREFERRED EMBODIMENTS

Figure 1:
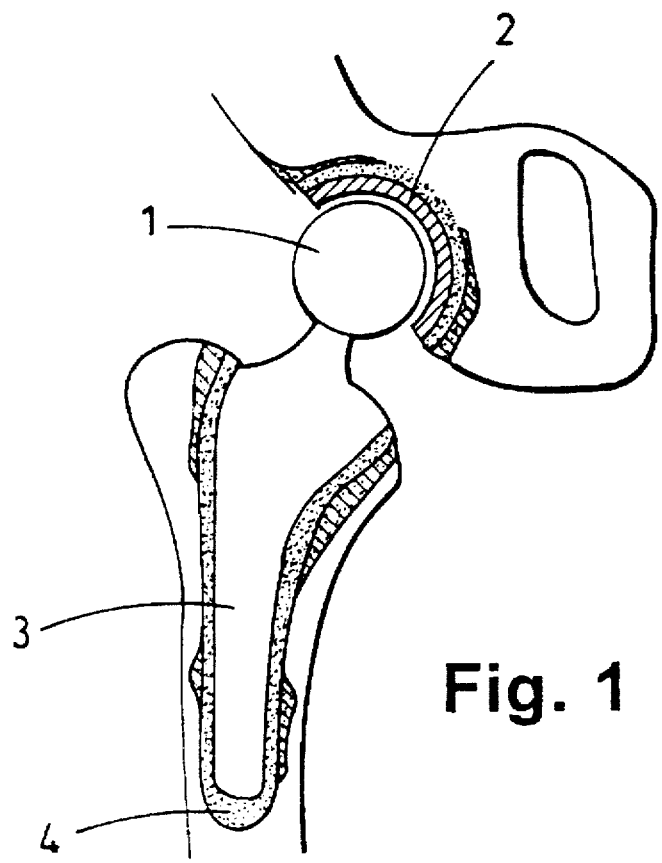
FIG. 1 is a diagrammatic view of a total hip prosthesis illustrating the problem arising from long-term wear in the prosthesis.
Figure 2:
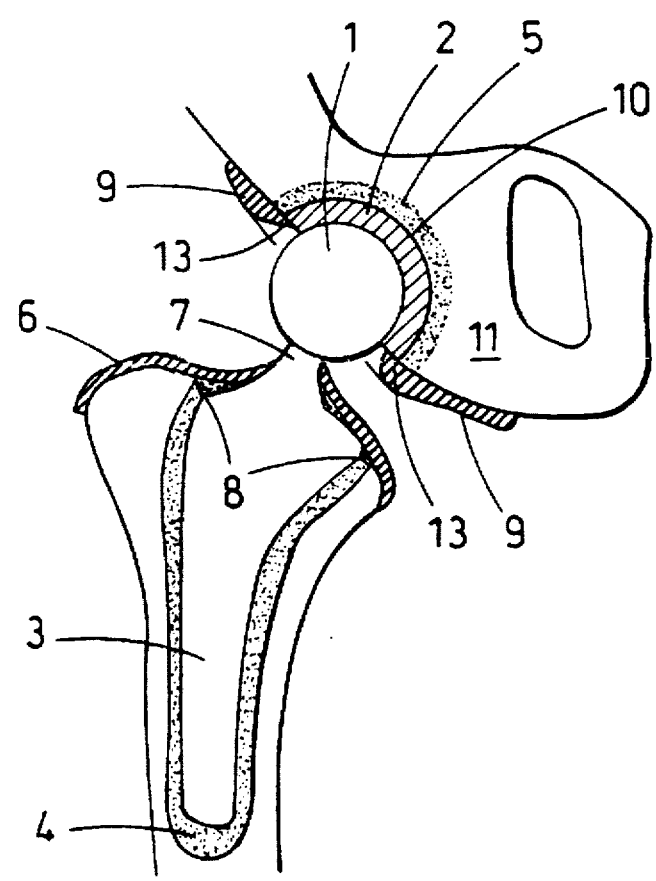
FIG. 2 is a view similar to FIG. 1 and illustrates the solution provided by the present invention.

Referring to FIGS. 1 and 2, articulating movement of the ball 1 in the acetabulum insert 2 causes wear particles to be generated which are released into the space within the joint and are pumped by such articulating movement into fissures or openings between the intramedulary canal and the stem of the femoral implant. Similar ingress of wear particles takes place between the acetabulum and the hemispherical socket implant 2. After a period of time, such wear particles migrate along the cement/metal interface and lodge in areas where they initiate endosteal erosion of the bone. Ultimately, the joint becomes so loose that a revision operation is necessary. The solution is illustrated in FIG. 2, in which a femoral implant having a stem 3 is installed in a femur using a cement mantle 4 and a socket 2 is similarly installed using a mantle of bone cement 5 in the acetabulum. The proximal end of the femur is covered with a microporous membrane 6, which is cut to size to fit snugly around the neck 7 of the femoral implant so that it covers the junction 8, between the bone canal and the implant, thus providing a primary seal against the ingress of wear particles. Similarly, the socket 2 is provided with a ring-like shaped membrane 9, covering the junction 10 between the socket 2 and the acetabulum 11. Obviously a gap must be left so that free movement and articulation of the ball 1 in the socket 2 is not interfered with but some secure attachment of the edge 13 of the membrane to the socket member 2 is highly desirable. This may be achieved, for example, by welding e.g. by ultrasonic welding of the membrane to the plastic material of the socket 2.

However, it may be possible to securely attach the ring or collar 9 of membrane material to the surrounding area of the bone sufficiently securely by suturing or stapling. Another method of attaching the membrane to the socket member is by means of an adhesive. Suitable synthetic polymeric adhesives include thermosetting adhesives such as acrylates, epoxy and polyester resins, glass ionomer or polyurethanes.

Figure 3:
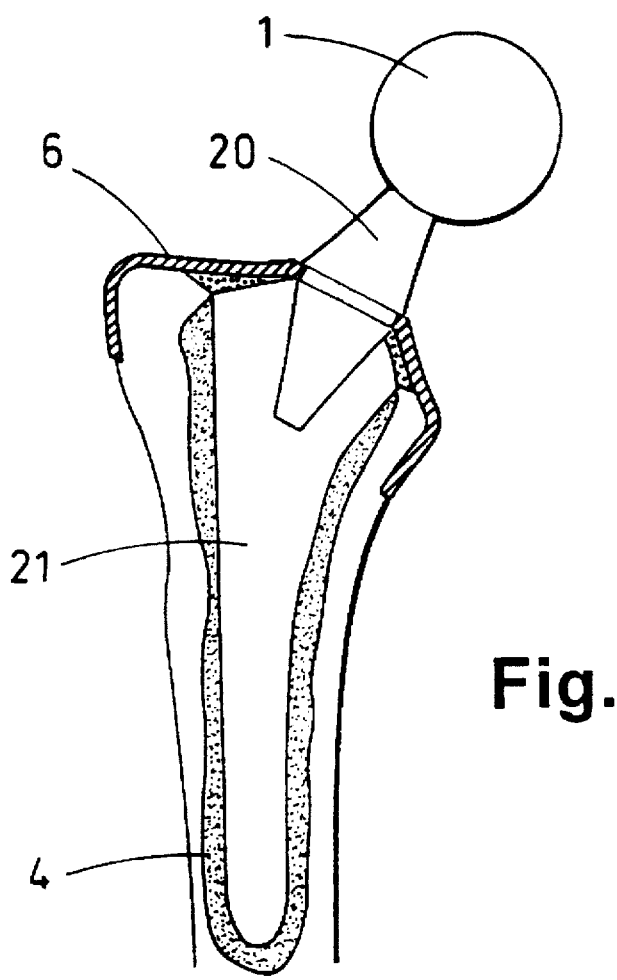
FIG. 3 is a further view similar to FIG. 2 but showing additional details as to the manner in which the membrane may be attached.
Figure 4:
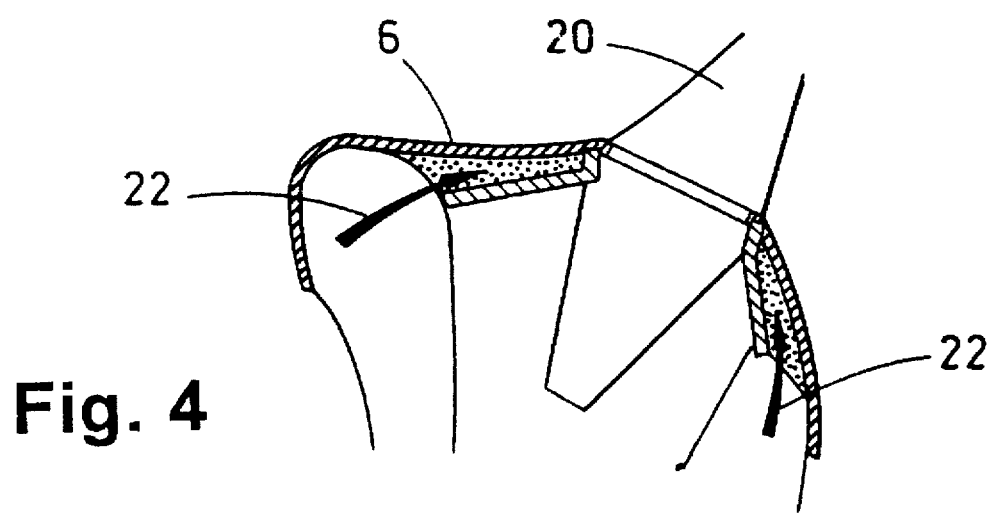
FIG. 4 is a partial view, slightly enlarged, of the proximal part of the stem of the implant shown in FIG. 3.

FIGS. 3 and 4 show variations in the method of attachment of the membrane over the proximal end of the femoral stem and femur. As can be seen in FIG. 3, the membrane 6 is secured to the neck of the femoral implant by trapping it between a separate neck component 20 and the stem 21. In the arrangement illustrated in FIG. 3, the neck portion is a taper fitting to the femoral stem.

In another possible embodiment, the neck portion is threaded and fits into a threaded socket within the stem, screwing of the neck portion into the stem also trapping the inner edge of the membrane and thereby securing the membrane to the femoral implant. The periphery of the membrane 6 extends past the junction between the canal and the implant and is attached firmly to the bone by stapling or suturing or by means of an adhesive, such as one of those mentioned above. Photocurable resin adhesives such as those used in dentistry may also be employed in order to increase the speed of attachment to the bone.

FIG. 4 illustrates an additional benefit of the invention. By selecting a membrane 6, whose pore openings are sized so as to exclude connective tissue cells, the conditions necessary for bone growth are encouraged beneath the membrane so that after a period of time, bone will grow from the upper end of the femur in the direction of the arrows 22 over the junction between the stem of the femoral implant and the bone canal. This will have the dual effects of further locking the implant firmly into position and, also, providing a permanent seal preventing further ingress of wear particles caused by articulation of the joint components. It will be appreciated, therefore, that the invention is applicable to cases where the prosthesis does not include any articulating parts. In such cases, there is a benefit in encouraging bone regeneration. This is particularly applicable in the case of revision prostheses.

As explained above, the membranes employed in the present invention are preferably bio-compatible microporous membranes which are manufactured by the process described in the above cited U.S. Patents. The membrane will preferably have a thickness between about 0.05 to 0.25 mm, especially about 0.08 to 0.2 mm, e.g. 0.1 to 0.18 mm.

The membrane may be a composite structure. For example, the portion of the membrane in contact with the prosthesis or overlapped onto the surrounding bone may be laminated to a plastics material which is more readily bonded to the bone or the metal of the prosthesis. Such plastic materials can be laminated to the microporous membrane by heat and pressure, with or without an adhesive.

Although the invention as described above employs a semi-permeable membrane, it is possible to use instead an impermeable membrane where the objective is solely to exclude wear particles from the implant/bone interface. In such cases, the membrane may be a continuous film of a biocompatible sheet material, preferably a fluorinated olefin, such as P.T.F.E.

We claim:

1. A method of sealing an interface between an articulating prosthesis and a bone into which one component of the prosthesis is implanted which comprises:

applying over a junction between said component and the bone a membrane having a microporous structure, whereby liquids are able to pass through the membrane but wear particles generated by mechanical wear of said prosthesis are not able to pass through the membrane; and securing the membrane to the bone in an area surrounding the component and securing the membrane to the component so as to cover the junction.

2. The method according to claim 1, further including the step of selecting the membrane wherein the openings in the microporous membrane are sized so as to exclude connective tissue cells, whereby bone regeneration under the membrane is encouraged.

3. A method according to claim 2 wherein the membrane is a microporous fluorinated polymer.

4. A method according to claim 2 wherein the membrane is secured to the prosthesis and attached to the surrounding bone beyond the area of the junction between the prosthesis and the bone.

5. The method according to claim 1, wherein the membrane is fixed to said component of the prosthesis and to the bone by means of an adhesive.

6. A method according to claim 1, wherein the junction comprises the interface between said component and the bone, and the membrane extends over an end of said interface in a direction substantially perpendicular to the interface.

* * * * *